United States Patent [19]

Loge et al.

[11] Patent Number: 5,474,449

[45] Date of Patent: Dec. 12, 1995

[54] LASER TREATMENT UNIT ESPECIALLY FOR MEDICAL OR DENTAL PURPOSES

[75] Inventors: Hans Loge, Biberach; F. H. Uwe Mohn, Schelklingen, both of Germany

[73] Assignee: Kaltenbach & Voigt GmbH & Co., Biberach/Riss, Germany

[21] Appl. No.: 11,308

[22] Filed: Jan. 29, 1993

[30] Foreign Application Priority Data

Jan. 29, 1992 [DE] Germany .............................. 9201056 U
Apr. 3, 1992 [DE] Germany ........................... 42 11 233.8

[51] Int. Cl.$^6$ .............................. A61C 1/00; A61C 3/00; A61C 1/08
[52] U.S. Cl. ................................... 433/29; 43/126; 606/19
[58] Field of Search ............................ 433/29, 126, 215; 606/10, 13, 14, 15, 16, 17, 18, 19

[56] References Cited

U.S. PATENT DOCUMENTS

| | | | |
|---|---|---|---|
| 3,913,582 | 10/1975 | Sharon | 606/10 X |
| 4,398,885 | 8/1983 | Loge et al. | 433/29 X |
| 4,431,412 | 2/1984 | Lares et al. | 433/29 |
| 4,473,074 | 9/1984 | Vassiliadis | 606/10 X |
| 4,504,227 | 3/1985 | Lohn | 433/126 |
| 4,578,034 | 3/1986 | Shibata et al. | 433/29 |
| 4,642,051 | 2/1987 | Lohn | 433/126 X |
| 4,725,232 | 2/1988 | Hatakeyamn | 433/126 X |
| 4,826,431 | 5/1989 | Fujimura et al. | 433/29 |
| 5,074,785 | 12/1991 | Malata, Jr. | 433/29 |
| 5,136,676 | 8/1992 | Arnett et al. | 606/19 X |

FOREIGN PATENT DOCUMENTS 3232007 9/1981 Germany .
4030734 4/1991 Germany .

*Primary Examiner*—Nicholas D. Lucchesi
*Attorney, Agent, or Firm*—Scully, Scott, Murphy & Presser

[57] ABSTRACT

A dental laser treatment unit, especially for medical or dental purposes having a control unit and a supply device, connected with the control unit by a releasable connection, for a laser treatment instrument. Two medium lines are provided, which lines issue from the control unit, extend through the releasable connection and along the supply device to the laser treatment instrument and with the laser treatment instrument being connectable with the supply device likewise by a releasable connection, the releasable connection between the control unit and the supply device and/or between the supply device and the laser treatment instrument is formed by a plug-in coupling, which automatically engages and disengages elastically, having a cylindrical coupling peg and a cylindrical coupling bushing which receives the peg, with the medium line for the laser beam extending coaxially through the plug-in coupling and the further medium line passing through the cylindrical separating line between the coupling peg and the coupling bushing in a sealed manner, and continuing in the coupling peg and in the coupling bushing, and with there being provided next to the mouth opening at the separating line an annular groove in the inner wall of the coupling bushing or preferably in the outer wall of the coupling peg.

21 Claims, 10 Drawing Sheets

LASER TREATMENT UNIT ESPECIALLY FOR MEDICAL OR DENTAL PURPOSES

TECHNICAL FIELD OF THE INVENTION

Background of the Invention and Prior Art

There are two essential requirements for a medical or dental laser treatment unit. On the one hand, a large laser beam capacity is desired in order to be able to carry out the treatment efficiently and, on the other hand, operator-friendly and easy guidance of the treatment, for example, instrument is desired. The latter is of significance in particular because the operator does not feel any resistance to treatment during treatment of a tooth with a laser beam, as is the case with mechanically acting treatment instruments, for example a drill which is pressed against the surface to be worked during the drilling with a certain force of pressure.

Laser treatment units are known which are set up to provide for treatment instruments which contain the laser beam-generating device so that the energy required for the laser beam-generation is to be supplied to the hand pieces from the control unit associated with the laser treatment unit. Such laser treatment instruments are of a complicated design and are also large in terms of construction and have a great weight. Moreover, one laser beam-generating device has to be associated with each pertinent laser treatment instrument, this resulting in high costs of production.

A laser-treatment unit has been proposed, in which the laser beam-generating device is integrated into the control unit. With such a construction, it is necessary to guide the laser beam from the control unit to the laser treatment instrument. A flexible light-conducting cable can be used for this. Usual screw connections are used for the connection of such a supply device to the control unit.

It has already been proposed to utilize the rotatability of the first link of an articulated link-arm, which carries the laser treatment instrument, for the rotatability of a laser treatment instrument about its longitudinal axis. In the case of this proposal the laser hand piece is connected with the first link of the articulated link-arm by means of a connection piece which has a connection thread on both sides and in this way can be screwed together both with the laser hand piece and with the arm link. Moreover, in the case of this proposal a lens for the laser beam is arranged in the connection piece. A medium line is provided in an arrangement which bridges the connection piece. For this, located in the rear end region of the laser hand piece there is a small connection tube, which projects from the outer lateral surface of said hand piece, for a small medium hose which bridges the connection piece. The medium line extends within the laser hand piece to a nozzle which is arranged in the vicinity of a lateral outlet opening for the laser beam.

In the case of this laser treatment instrument according to the proposal, the rotatability thereof is impaired, because, on the one hand, the arm link is moved as well and, on the other hand, the rotatability is limited by the presence of the medium hose which is wound around the connection piece in the event of rotation. If the medium hose is very long, rotatability about 360° could perhaps be achieved, yet this would result in a medium hose loop which impairs the handling of the laser treatment instrument.

OBJECT OF THE INVENTION

The object of the invention is to configure a laser treatment unit of the kind specified at the beginning such that, with simple construction and efficient media supply, a connection of the laser treatment instrument to the supply device and/or of the supply device to the control unit is possible with ease of operation.

SUMMARY OF THE INVENTION

According to the present invention there is provided a laser treatment unit having a control unit and a supply device, connected with the control unit by means of a releasable connection, for a laser treatment instrument having an outlet, preferably at the side, at its front end for a laser beam, with at least two medium lines being provided, which lines issue from the control unit, extend through the releasable connection and along the supply device to the laser treatment instrument and of which one is intended for the supply of a laser beam and the other is intended for a further medium, in particular air and/or water, and the laser treatment instrument being connectable with the supply device likewise by means of a releasable connection, wherein the releasable connection between the control unit and the supply device and/or between the supply device and the laser treatment instrument is formed by means of a plug-in coupling, which automatically engages and disengages elastically, having a cylindrical coupling peg and a cylindrical coupling bushing which receives the peg, with the medium line for the laser beam extending coaxially through the plug-in coupling and the further medium line passing through the cylindrical separating line between the coupling peg and the coupling bushing in a sealed manner, and continuing in the coupling peg and in the coupling bushing, and there being provided next to the mouth opening at the separating line an annular groove in the inner wall of the coupling bushing or preferably in the outer wall of the coupling peg so that it is possible to rotate by 360° and more the supply device relative to the control unit and/or the laser treatment instrument relative to the supply device without interruption of the medium line.

In the case of the laser treatment unit according to the invention, provided between the control unit and the supply device and/or between the supply device and the treatment instrument there is a plug-in/rotary coupling which not only renders possible easy rotation of the supply device at the control unit and/or easy rotation of the laser treatment instrument at the supply device, but also establishes a rapid-action coupling or plug-in connection with ease of operation so that the supply device and/or the laser treatment instrument can be easily and quickly coupled and uncoupled again, for example in order to disinfect or service the supply device and/or the laser treatment instrument or to exchange it/them for another function mode.

In this regard ease of rotation is ensured, something which is desirable for operating reasons during the treatment. The media lines are guided through the plug-in/rotary coupling and they are automatically connected or separated when coupling and uncoupling.

In the case of the configuration according to the invention, a connection of the medium line at the periphery of the laser treatment instrument or its hand piece respectively is not necessary, as the medium line does not bridge the coupling point, but is guided through it. In the case of such a configuration according to the invention, easy rotation of the laser hand piece is also possible, because the connection piece and the medium line section located behind the plug-in/rotary coupling are not moved as well. This also applies to the first arm link of an articulated link-arm when the laser treatment instrument according to the invention is to be connected with such an articulated link-arm.

It is possible, within the scope of the invention, to provide various supply devices which can be connected to the control unit and/or with the laser treatment instrument rapidly and with ease of operation. Such supply devices can be an articulated link-arm, through which a laser beam can be guided by means of an optical conducting system, or they can also be flexible supply hoses in the form of light conductors. In this regard, it is possible to use such hose-shaped light conductors in which the laser beam is guided through a glass fibre conductor or through a conductor channel containing a fluid or it is even possible to use such a hose-shaped light conductor in which the laser beam is guided through a conductor channel, the inner wall of which is mirror-coated.

In preferred embodiments of the invention features are provided which ensure precise guidance of a laser beam, in particular in the region of the plug-in/rotary couplings, ensure coaxial guidance of a laser beam, result in a small, simple, light, expedient construction which can be produced in a cost-favourable manner and, moreover, facilitate and improve the installation and removal and also the handling during the treatment.

BRIEF DESCRIPTION OF THE DRAWINGS

The invention and further advantages which can be achieved by it are explained in greater detail in the following with the aid of preferred exemplary embodiments and the drawings.

DETAILED DESCRIPTION OF PREFERRED EMBODIMENTS ACCORDING TO THE INVENTION

Figure 1:
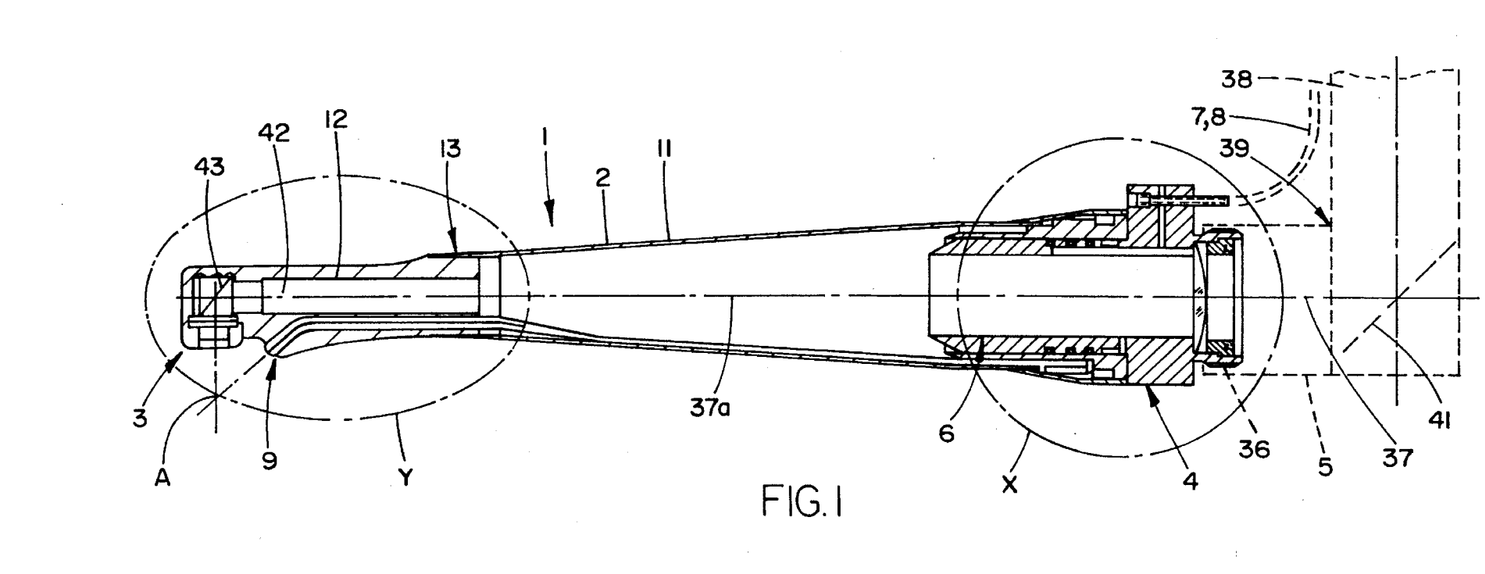
FIG. 1 shows a laser treatment instrument according to the invention in longitudinal section.
Figure 2:
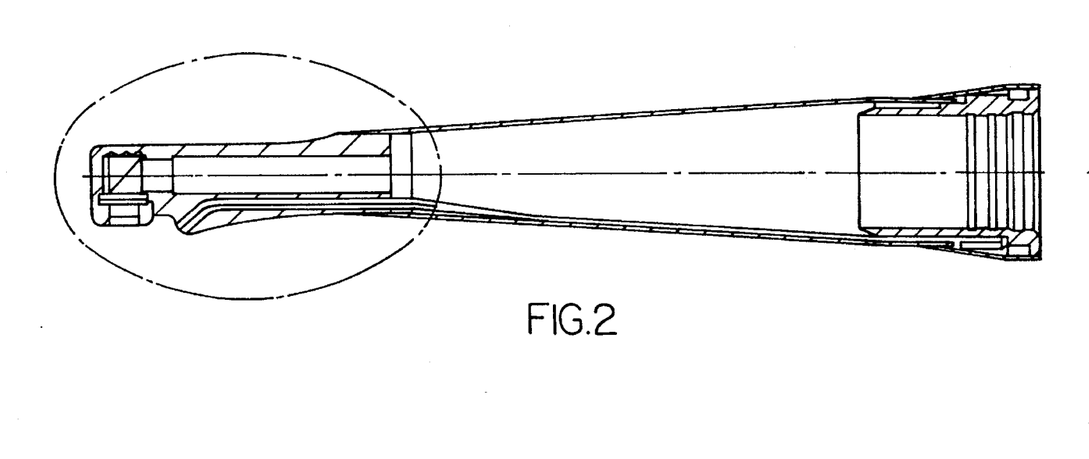
FIGS. 2 and 3 show a hand piece and a connection piece of the laser treatment instrument in longitudinal section.
Figure 3:
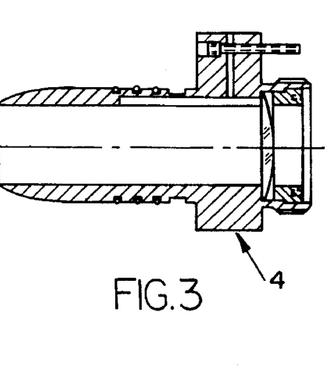

The main portions of the laser treatment instrument 1 are a hand piece 2 formed by a grip sleeve with an outlet 3 for a laser beam at its front end, a connection piece 4, by means of which the hand piece 2 is connected or can be connected with the first arm link 5 of an articulated link-arm which is not represented further, a plug-in/rotary coupling 6 for the releasable connection of the hand piece 2 with the connection piece 4, means 41, 31, 43 for conducting the laser beam axially through the connection piece 4 and the hand piece 2 to the outlet 3 of the latter and at least one, preferably two, media lines 7, 8, for water and compressed air, which are connected to the connection piece 4 and extend through the connection piece 4, the plug-in/rotary coupling 6 and the hand piece 2 to a preferably common media nozzle 9 which is arranged at a short distance behind the laser beam outlet 3.

The hand piece 2 is formed in two portions in the present configuration with a rear sleeve portion 11 and a front sleeve portion or head portion 12 and is plugged together at the point of separation 13. In this regard, the head portion 12 is firmly plugged into the sleeve portion 11 with a peg so that it is not releasable for ordinary operation. The point of separation 13 is preferably provided for reasons of ease of manufacture and assembly. At the rear end of the hand piece 2 the sleeve portion 11 is extended by means of an end sleeve piece 14 which has somewhat larger dimensions in cross section, engages over an outer shoulder at the rear sleeve edge and in which a bearing sleeve 15 is firmly inserted, the front end of which sleeve projects into the rear end region of the sleeve portion 11. The cylindrical inner wall of the bearing sleeve 15 forms a plug-hole 17 into which a coaxial, hollowly cylindrical plug-in peg 18 of the connection piece 4 can be plugged with little clearance for motion and can be elastically engaged in the plugged-in position. A radially acting, split spring ring 19 is used for this purpose, which ring sits in a peripheral groove 21, arranged in the rear region of tale plug-in peg 18, with clearance for movement and is thereby dimensioned to be so large that its outer casing projects slightly beyond the outer lateral surface 22 of the plug-in peg 18. When plugging the plug-in peg 18 into the plug-hole 17, the spring ring 19 is compressed. In the end plugged position it engages elastically into a corresponding inner peripheral groove 23 in the rear region of the bearing sleeve 15. When the plug-in/rotary coupling 6 thus formed is released as a result of exertion of a slight, axial force, excess pressure is applied to the spring ring 19, this being made possible or facilitated by stop slopes on the spring ring 19 and/or on the inner wall 16.

The plug-in peg 18 projects coaxially towards the front from a flange 24 which has a radial extension 25. At the rear, there projects from the flange 24 towards the rear a coaxial bearing ring 26 which on its outer lateral surface has an outer thread 27 and in the region of the rear half of its inner lateral surface has an inner thread 28. The front half of the inner lateral surface forms a cylindrical fitting hole 29 into which an optical lens 31 is inserted so as to fit, something which can best be seen from FIG. 4 (detail X). A shoulder 32, which is preferably planar, is used to mount the lens 31 axially between the fitting hole 29 and the cylindrical through-hole 33, which has somewhat smaller dimensions in cross section, in the connection piece 4 extending through the flange 24 and the plug-in peg 18. A ring nut 34, which is provided with an outer thread and with rotary working elements, which are at the rear and are not represented, for example small diametrically opposed holes, and with which the lens 31 is pressed against the shoulder 32 by means of a ring 35 arranged in between and made of elastic material such as, for example, rubber, is used to secure the lens 31.

The connection piece 4 is screwed with its outer thread 27 into a threaded hole 36 of the sleeve-form arm link 5 which is mounted such that it can be rotated about its longitudinal axis 37, coinciding with the longitudinal axis 37a of the hand piece 2, at a rear arm link 38 which extends transversely, preferably at right angles, relative to the first arm link 5 and which is likewise sleeve-form. In the case of the present configuration, the articulated link-arm, which is not represented in total, has several arm links in such a number and in such an arrangement that the mobility of the laser treatment instrument required for treatment is ensured. The laser beam is generated in a laser beam-generating device which is not represented and on which the rear end of the articulated link-arm is held. In this regard, the laser beam is conducted through the sleeve-form arm links. In the arm articulations, present between the arm links, here rotary articulation 39 between the arm links 5 and 38, the laser beam is deflected by means of a deflecting device, formed, for example, by means of a mirror or a prism 41, so that it emerges coaxially from the arm link 5 and extends in the direction of the longitudinal axis 37a through the lens 31, the through-hole 33 of the connection piece 4 and the hand piece 2. The hollow space of the sleeve-form hand piece 2, or a cylindrical channel 42 which is axial in the head portion 12, ends in an axial direction at the front end of the head portion 12 and then extends preferably at right angles towards the outside. Positioned in the region of this bend there is a laser beam-deflecting device, preferably a mirror or a prism 43, which refracts the laser beam preferably focused through the lens 31 in the prism 43 so that it crosses through the outlet 3 and meets in focus the treatment spot which is indicated with A and is located in the region of the point of intersection of the axes of the outlet 3 and the media nozzle 9.

It is advantageous to arrange the deflecting device such that it can be adjusted in order to be able to compensate for tolerance differences of the laser treatment instrument 1.

Figure 5:
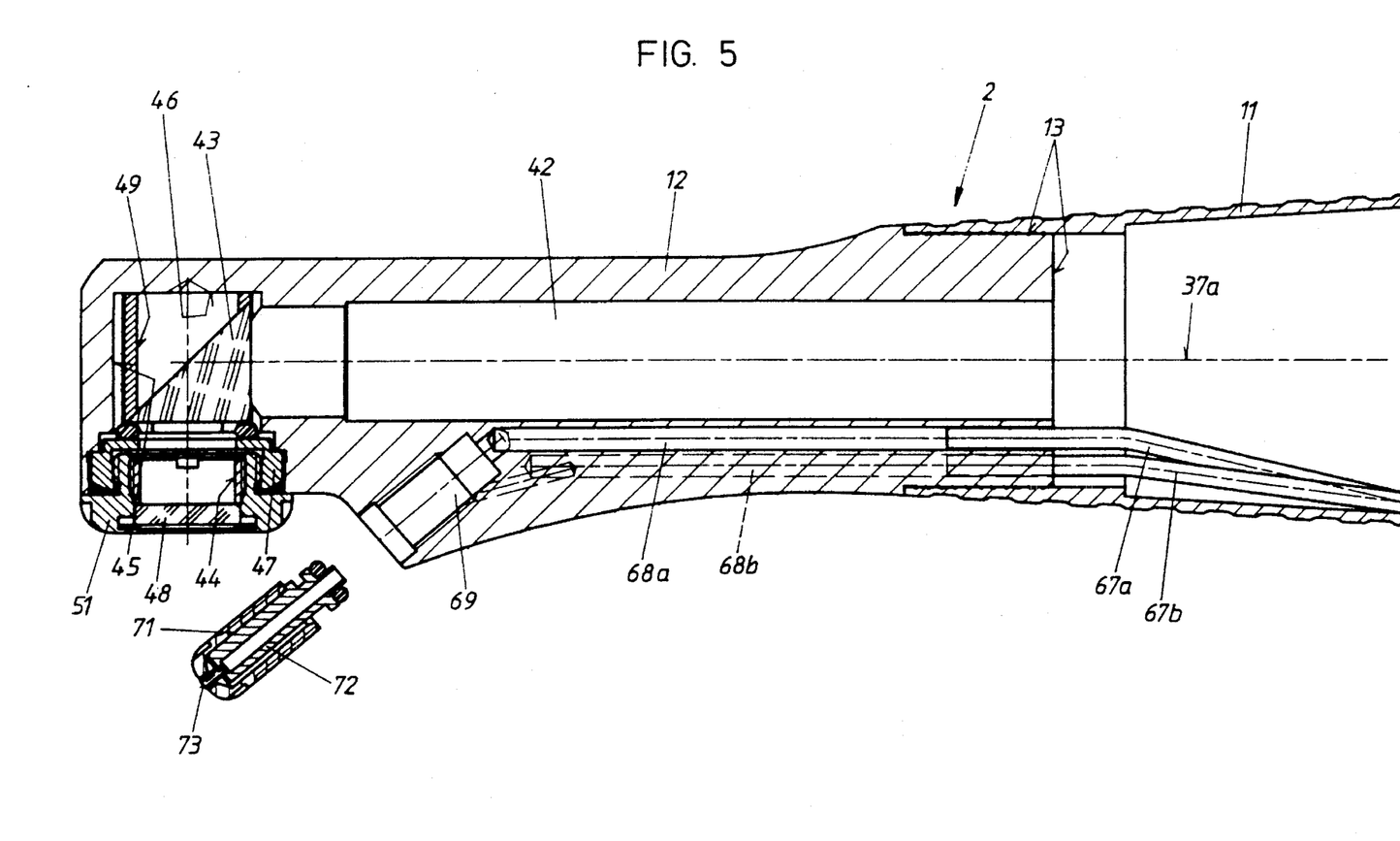
FIG. 5 shows an enlarged representation of the detail characterised in FIG. 1 by Y.

The prism 43 is preferably arranged or mounted according to FIG. 5, showing the detail Y, in an insert piece 49 which can be inserted in the sense of a cartridge into the transverse channel 45 forming the outlet 3 or into the end region of the channel 42. As FIG. 5 clearly shows, the fitting or insert piece 49 is pressed or tensioned against a preferably planar fitting surface 46 which preferably extends parallel to the longitudinal axis 37a and forms the base of the transverse channel 45. A ring nut 47 is used to hold the insert piece 49, which nut is screwed in the transverse channel 45 and preferably presses against the insert piece 49 by means of an elastic ring. In order to protect the deflecting device, formed by means of a mirror or the prism 43, from particles which chip off when treating a tooth with the laser beam, a protective disc 48, which is transparent to the laser beam, is arranged after said device and is held, such that it can be exchanged, in the region of the outlet 3 and can thus be replaced from time to time by a new one if, for example, it has become dull. The protective disc 48 can be made of glass or even plastics material. It is preferably secured in a holding ring 44 with outer thread, which ring can be screwed in the transverse channel 45 or into the ring nut 47, for which corresponding threads are to be provided. The holding ring 44 preferably has a flange 51 on the front side in which rotary working elements for the purposes of screwing in and out are provided, preferably formed by outer grooves. The screw-in depth of the ring nut 47 or of the holding ring 44 is preferably limited by a stop shoulder so that the insert piece 49 cannot be overloaded by the force of the contact pressure, but is pretensioned into its fitted position to a maximum extent by the elasticity of the previously described elastic ring.

Two media hoses 52a, 52b are provided for the media supply, which hoses extend along the articulated link-arm and are held for example externally on the latter. The media hoses 52a, 52b and further sections of the media lines generally denoted with 7, here two media lines, lie one behind the other in the view given in the drawing, so that in each case only one media line 7 is visible. The media hoses 52a, 52b are connected to the connection piece 4, in each case by means of a small connection tube 53a, 53b, which projects to the rear and is firmly inserted into an axis-parallel hole 54a, 54b in the extension 25. A channel 55a, 55b extends from the hole radially inwards as far as an axial channel 56a, 56b which extends towards the front as far as the region in front of the spring ring 19 and issues with a channel section 57a, 57b which extends radially outwards at the outer lateral surface 22 of the plug-in peg 18. In this regard, the channel sections 57a, 57b of the two media lines 7 which are staggered in the peripheral direction are arranged at an axial distance a from each other. A peripheral groove 58a, 58b is associated with and lies opposite each channel section 57a, 57b or its mouth opening respectively in the inner walk 16 of the bearing sleeve 15. There are provided for the purpose of axially sealing the channel sections 57a, 57b or peripheral grooves 58a, 58b respectively three sealing rings 59a, 59b, 59c of which in each case two are located axially in front of and behind the pertinent channel section 57a, 57b or the pertinent peripheral groove 58a, 58b respectively. The sealing rings, which are preferably formed by O-rings, are each located in a peripheral groove which is preferably arranged in the outer lateral surface 22 of the plug-in peg 18. There branches off from the peripheral grooves 58a, 58b in each case a radial channel section 61a, 61b which in each case corresponds with a pertinent radial section 62a, 62b in an insert piece 63 which sits in a pertinent recess 64 or in a pertinent hole in the bearing sleeve 15. Each radial channel section 62a, 62b communicates with an axial channel section 65a, 65b in the insert piece 63 which issues at the front side of the latter. The axial channel sections 65a, 65b are likewise arranged so as to be staggered in the peripheral direction. The separating lines between the radial channel sections 61a, 61b and 62a, 62b belonging to each other are each sealed by means of a sealing ring 66a, 66b which is arranged in a groove in the preferably planar base surface of the recess 64 or in the inner surface of the insert piece 63 facing it.

A small tube 67a, 67b is firmly and tightly inserted into the front-side mouth opening of each axial channel section 65a, 65b. The small tubes direct the pertinent medium (compressed air, water) to the media nozzle 9.

In the case of the present configuration, the front ends of the small tubes 67a, 67b are firmly and tightly inserted into the rear openings of axial channels 68a, 68b in a firm and tight manner, which channels extend to a nozzle bore 69 which accommodates the media nozzle 9 and the central axis of which is arranged obliquely, preferably at an angle of 45° relative to the longitudinal axis 37a. The media nozzle 9 has a sleeve-form outer nozzle portion 71 and a sleeve-form inner nozzle portion 72 which is accommodated in the latter, which portions can be screwed into the nozzle bore 69 as a structural unit with an outer thread arranged on the outer nozzle portion 71. The water is supplied coaxially to the inner nozzle portion 72 which is sealed by means of a sealing ring and the sleeve tip of which ends at a short distance before the common nozzle opening 73 of the nozzle outer portion 71. The compressed air is supplied to the nozzle opening 73 through an axial channel which extends between the outer nozzle portion 71 and the inner nozzle portion 72. There occurs in the free space or gap present in front of the nozzle opening 73 automatic mixing of the compressed air and of the water to form a mixture or spray which emerges from the nozzle opening 73.

The sealed course of the media lines 7 described above transversely through the separating line between the plug-in peg 18 forming a coupling peg and the plug-hole 17 forming a coupling bushing renders possible rotation of the hand piece 2 in the plug-in/rotary coupling 6 by 360° and more, without the fear of impairment. The plug-in/rotary coupling 6 described above also renders possible a large cross section of the through-hole 33, this being of benefit to the laser beam through-guidance and conduction.

Associated with one or both media lines 7, preferably the media line carrying water, there is an adjustable throttle valve 74 with which it is possible to adjust the flow quantity and/or the pressure, with which the pertinent medium emerges at the media nozzle 9. In the case of the present configuration, the throttle valve 74 is arranged in the extension 25. In this region it is easily accessible from outside with an adjusting tool. The throttle valve 74 can be arranged in an axial or radial channel which runs into the pertinent channel section of the media line 7 so that it, preferably valve bodies which can screwed in and out, can vary the pertinent media channel cross section. The throttle valve 74 preferably has a screw 74a which is sealed at its periphery by means of a sealing ring, is screwed into a radial or axial bore 75, the free end of which is preferably pointed and the head end of which has a tool working element for rotation purposes. The bore 75 is preferably arranged so as to be parallel to the longitudinal axis 37a and outside the periphery of the hand piece 2 and is an elongation of the water channel 54a passing through towards the front, so that the screw 74a is accessible from the front.

The screw tip can cooperate with the channel in the pertinent small tube 53a.

Figure 6:
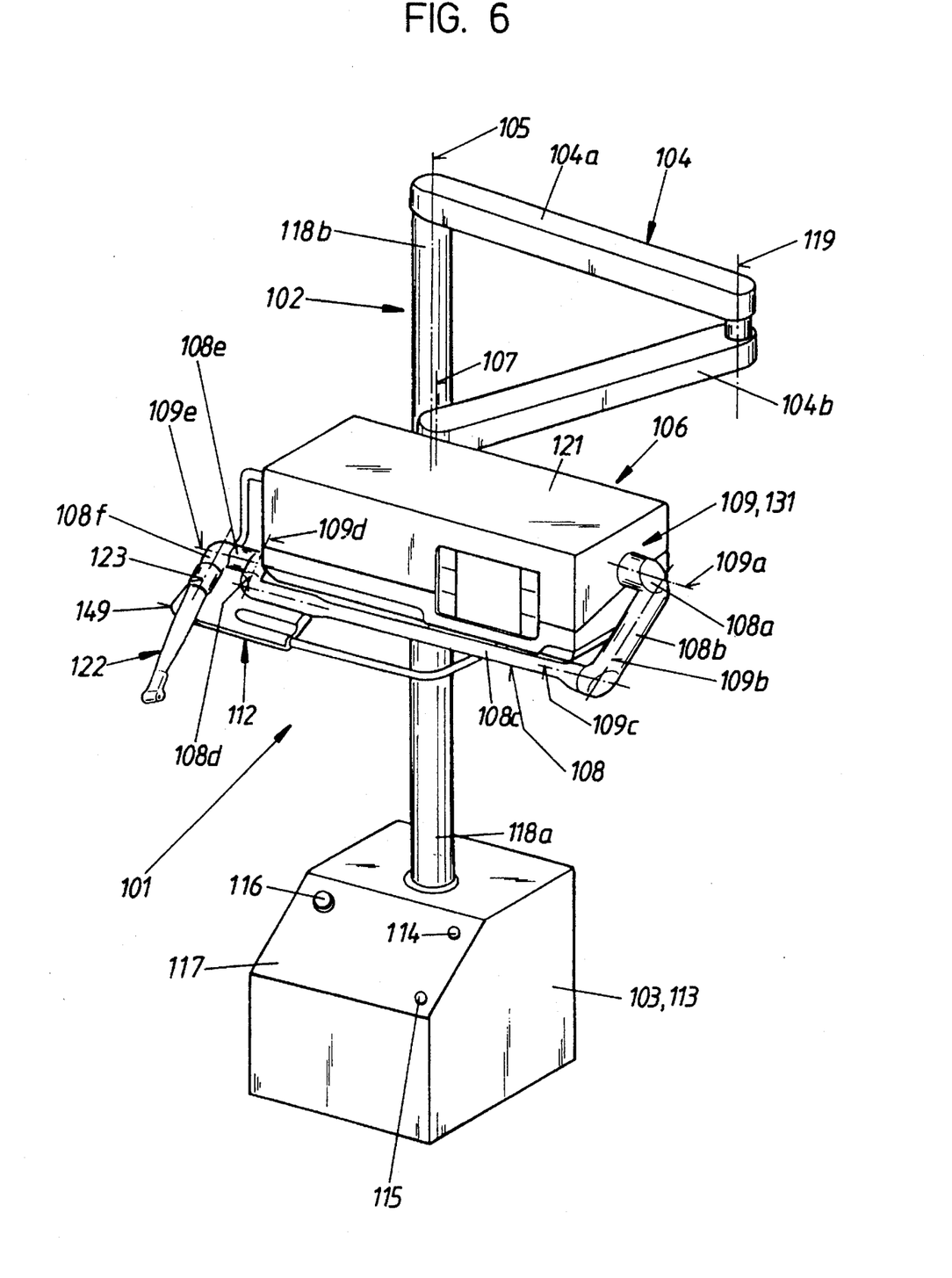
FIG. 6 shows a dental laser treatment unit according to the invention in a perspective front view.

The laser treatment unit 101 represented in FIG. 6 consists of a stand 102 with a stand foot 103, a generally horizontal supporting arm 104 which is mounted in a freely rotatable manner about a vertical axis of rotation 105 on the stand 102, a control unit 106 which is mounted such that it can be swung freely about a vertical axis of swing 107 at the free end of the supporting arm 104, an articulated link-arm 108 which is mounted in a freely rotatable manner about a horizontal axis of rotation 109a in a freely rotatable manner in a rotary bearing 109 of the control unit 106 and a supporting portion 112 held on the control unit 106 for the purpose of holding the free end region of the articulated link-arm 108 in the latter's not-in-use position.

In the case of the present configuration, the stand foot 103 is formed by means of a cube- or parallelepiped block-shaped box 113, on the front side of which and/or front upper side region of which electrical control elements are arranged. These can be a main switch 114, which can be preferably be locked by means of a lock, an on/off switch 115 and a safety cut-out switch 116, the last two preferably being push-button switches. It is advantageous to arrange the control elements on an oblique surface 117 which is provided in the upper front corner region of the box 113 and which extends obliquely upwards towards the rear. In such an arrangement, it is possible for the operator to operate the control elements 115 and 16 easily and reliably with the foot. A large part of the control device present is preferably arranged in the stand foot 103 forming a base part. In this regard, this can be a water storage container, a pump for the water supply, a laser network portion and a microprocessor.

The stand 102 preferably consists of a supporting column which is secured in or on the box 113 and which can preferably be telescoped, consisting of a lower column portion 118a, in which an upper column portion 118b is guided such that it can be displaced vertically and can be fixed in the respective position of sliding. The supporting arm 104 is preferably a so-called toggle lever arm having two arm portions 104a, 104b which are connected with each other at their facing ends in a toggle lever joint such that they can be swung about a vertical axis of swing 119.

The rotary bearing 109 is located on one side of the parallelepiped block-shaped housing 121 of the control unit 106 so that the axis of rotation 109a extends parallel to the front side of the laser treatment unit 101. In the case of right-hand execution (for right-handed people) the rotary bearing 109 is arranged on the right and the supporting portion 112 is located in the left end region of the control unit 106. A plate-shaped deposit portion can be used as a supporting portion 112 which is preferably arranged in the front corner region of the housing corner remote from the rotary bearing 109.

The articulated link-arm 108 consists of at least three arm links which are rotatably or swing-mounted about axes of rotation or swing which extend so as to be perpendicular to each other. In the case of the present configuration, the articulated link-arm 108 consists of six arm links, of which the first arm link 108a forms the arm-side bearing portion of the rotary bearing 109. The further arm links 108b, 108c, 108d, 108e and 108f are respectively mounted in a freely rotatable manner about an axis of rotation 109b, 109c, 109d, 109e, 109f, which extends at right angles to the previous axis of rotation, at the free end of the previous arm link in each case. Arranged at the free end of the leading arm link 108f there is a mechanical connection, in particular a screw connection preferably with internal thread, by means of which a laser treatment instrument 122 can be releasably secured to the articulated link-arm 108, and which may correspond to that according to FIGS. 1 to 5. The longitudinal central axis 123 of the laser treatment instrument 122 extends so as to be perpendicular to the axis of rotation 109. As a result, an advantageous arrangement for use in the mouth region of a patient is obtained.

Figure 7:
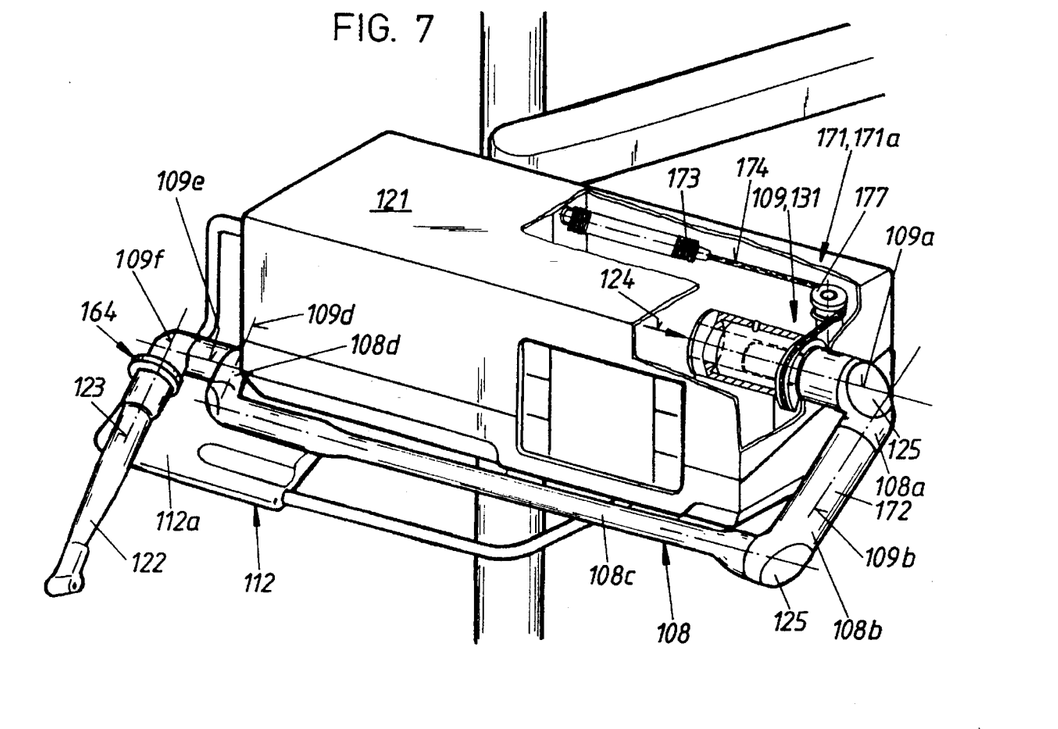
FIG. 7 shows the laser treatment unit in an enlarged sectional representation of the mounting of an articulated link-arm and of a compensating device for the self-weight of the articulated link-arm.

Located in the control unit 106 there is a laser beam-generating device which is not represented in detail and which directs the laser beam, illustrated in FIG. 7 by an arrow 124, coaxially through the rotary bearing 109, that is, coaxially to the axis of rotation 109a, into the articulated link-arm 108. For this purpose, the rotary bearing 109 is formed so as to be hollow. The arm links 108a to 108f are also formed so as to be hollow for the through-guidance of the laser beam 124, with a light-conducting system integrated into the through-channel of the hollow articulated link-arm 108, with which system the laser beam 124 is conducted to the free end of the articulated link-arm 108 and can be introduced coaxially into the laser treatment instrument 122. The optical conducting system has, in the articulations, which are present between the arm links 108a to 108f, mirrors 125 or prisms which are represented only schmatically and which effect a deflection of or refract the laser beam 124 by, in each case, 90° in the longitudinal direction of the articulated link-arm 108. The mirror 125 or the prism is secured in each case to the previous arm link, in which case it refracts the laser beam 124 in the longitudinal direction of the subsequent arm link.

The articulated link-arm 108 is releasably connected with the control unit 106 by means of a plug-in coupling 131 which is formed as a rapid-action coupling. The plug-in coupling 131 comprises a cylindrical coupling peg and a cylindrical coupling bushing which receives it with little clearance of motion. In the case of the present exemplary embodiment, the coupling peg 132 is provided on the last arm link 108f so as to be in one piece therewith or as an add-on portion thereof (FIG. 8), in which case with a non-one piece execution the coupling peg 132 can be screwed together with the last arm link 108f, for which purpose it is possible to use an outer thread 133 on a coaxial sleeve projection 134, with which the coupling peg 132 can be screwed into an inner thread (not represented) of the arm link 108f. The peg section 132a of the coupling peg 132 extends coaxially from a flange 135 towards the rear, from the other side of which the sleeve projection 134 extends towards the front. The coupling peg 132 has passing through it a cylindrical through-hole 136 so that the peg section 132a is sleeve-form. The front outer edge of the coupling peg 132 is rounded in order to facilitate the plugging-in thereof into the coupling bushing 137. The plug-in coupling 131 can be elastically engaged in the closed position of its coupling portions and can be released by exerting excess pressure to overcome the engagement with axial movement of the movable coupling portion. A radially effective, split spring ring 139 is used for this, which ring sits in a peripheral groove 141 arranged in the rear region of the peg section 132a of the plug-in peg 132 with clearance for movement and thereby has such dimensions that its outer lateral surface projects beyond the outer lateral surface 142 of the plug-in peg 132. When plugging the plug-in peg 132 into the plug-hole 143 of the coupling bushing 137, the spring ring 139 is compressed. In the end plugged position it engages elastically into a correspondingly shaped inner peripheral groove 144 in the front region of the coupling bushing 137. When the thus formed plug-in/rotary coupling 131 is released by exertion of a comparatively slight, axial force, excess pressure is exerted to overcome the spring ring 139, this being made possible or facilitated by stop slopes on the spring ring 139 and/or on the inner wall of the plug-hole 143.

Figure 8:
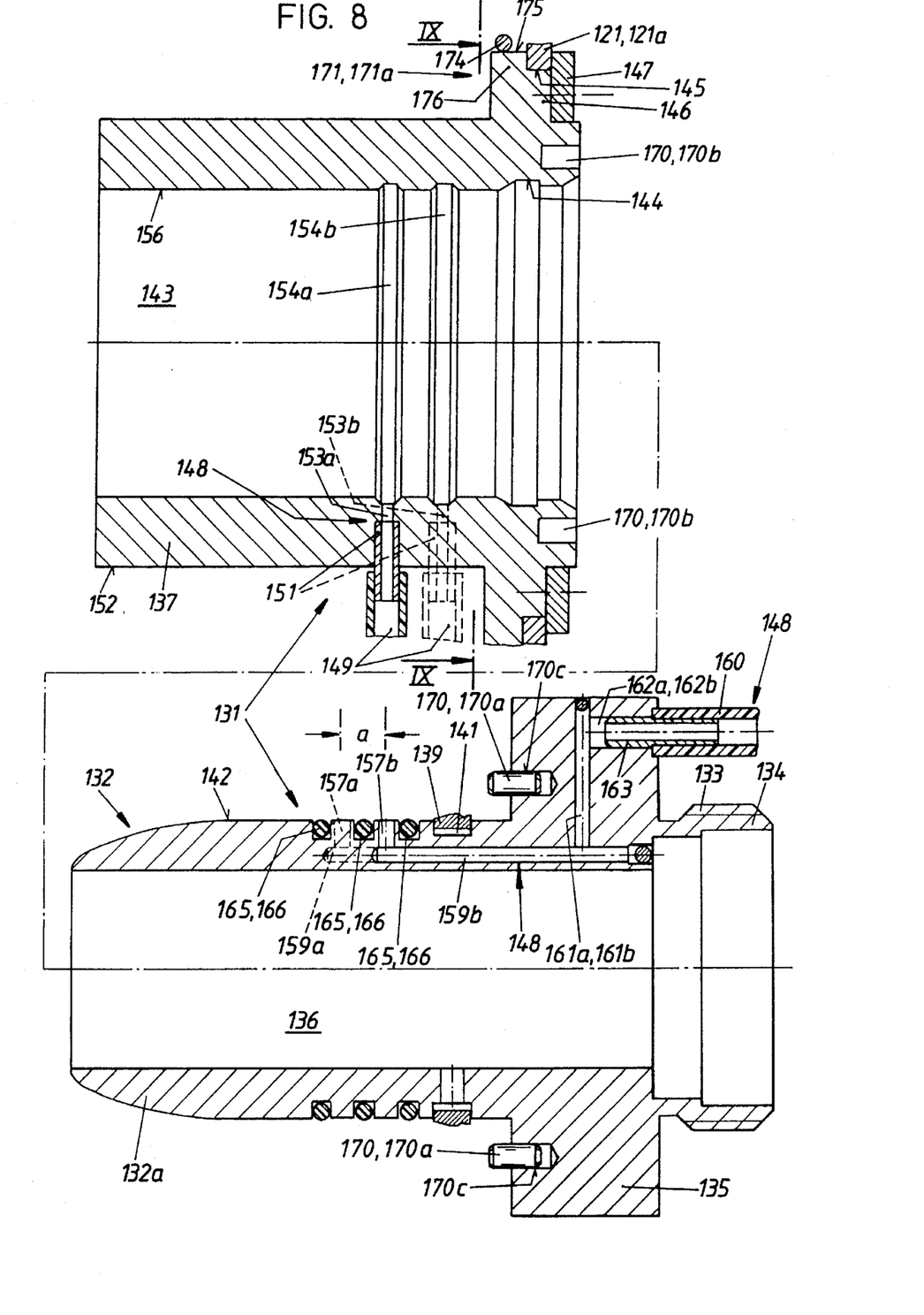
FIG. 8 shows a rotary bearing/plug-in coupling combination in vertical section.

The coupling bushing 137 forms the rotary bearing portion of the rotary bearing 109 associated with the articulated link-arm 108. The rotary bearing portion, which is associated with the control unit 106, can be mounted, for example, on the lateral housing wall 121a of the housing 121. In the case of the present configuration, there is provided in the lateral housing wall 121a a round hole 145 into which a cylindrical ring extension 146 coaxially projecting from the coupling bushing 137 is set with little clearance for movement. A bearing disc 147 is used for the axial securement of the coupling bushing 137 in the hole 145, which disc rests against the planar end face of the ring extension 146, and also with that is secured, for example, by screws and projects over the outside hole edge of the hole 145. The coupling bushing 137 is thus securely mounted in the hole 145 and is thereby freely rotatable.

In addition to the laser beam-conducting system, further media lines for the supply of media are provided for the purpose of supplying the laser treatment instrument 122, which lines extend through the rotary bearing 109 and the plug-in coupling 131 and also along the articulated link-arm 108 and in the front end region of the latter can be connected to the laser treatment instrument 122. Such further media can be water, air, water-air mixture, electric current and/or a so-called pilot beam. Two media supplies, in particular for air and water or water-air mixture each in one of two media lines 148 are described in the following by way of example. In contrast to the laser beam, for which no seal is required when guiding it along the articulated link-arm 108 and through the rotary bearing 109 and the plug-in coupling 131 and which is preferably arranged so as to be coaxial to the rotary bearing 109, in the case of media lines for treatment air and/or fluid, such as in particular water or spray, a sealed supply is required, in particular in the region of the plug-in coupling 131 and the releasable connection between the first arm link 108f and the treatment instrument 122 which is preferably likewise formed by means of a rapid-action or plug-in coupling. These media lines 148 extend from the pump arranged in the stand foot 103 or from a pump arranged in the control unit 106 to the coupling bushing 137, in which case they can be flexible media hoses 149 which can be connected with line connections 151 at the coupling bushing 137, for example, by being plugged thereon. In the case of the present configuration, the line connections 151 are located at the outer lateral surface 152 of the coupling bushing 137 and in each case a media channel 153a, 153b is guided radially inwards to a pertinent annular groove 154a, 154b, in the inner lateral surface 156 of the coupling bushing 137, at an axial distance a from each other. Provided in the coupling peg 132 there are respective short radial channel sections 157a, 157b which pass through the outer lateral surface 142 of the coupling section 132a in the radial plane of the pertinent annular groove 154a, 154b and thus communicate therewith. Within the wall of the coupling peg 132 channel sections 159a, 159b extend from the channel sections 157a, 157b parallel to the longitudinal central axis of the coupling peg 132 towards the outside. Connected to the axial channel sections 159a, 159b there are channel sections 161a, 161b which extend in the flange 135 radially towards the outside and of which only one is visible and from which axis-parallel channel sections 162a, 162b issue, extending towards the outside and emerging on the front side of the flange 135. The channel sections described above are formed by bores, with the channel sections 159a, 159b being bored from an inner shoulder of the through-hole 136 of the coupling peg 132 and the channel sections 161a, 161b being bored from the peripheral surface of the flange 135 and being closed at the end by stoppers. The channel sections 162a, 162b have greater dimensions in cross section and hose-connection elements, here connection sleeves 163, are firmly inserted therein, located at a distance of a few millimeters next to the pertinent arm link 108f. Plugged onto the two connection sleeves 163 which are present there are two flexible media hoses 160 which extend along the articulated link-arm 108 to the front end of the latter for the purpose of supplying the laser treatment instrument 122 and are held on the articulated link-arm 108, for example by bandages. The laser hand piece is connected with the first arm link 108f such that it can be released by means of a plug-in/rotary coupling 164 which is comparable with the plug-in/rotary coupling described above. Provided at this coupling point there is preferably a coupling peg which projects towards the front and which can be plugged into a coupling bushing of the laser hand piece and is screwed at its rear end together with the leading arm link 108f. This coupling peg, which is not represented in detail, is arranged in a mirror-inverted manner relative to the coupling peg 132 and is formed so that the screw connection and the through-guidance of the media lines 148 can be effected through the existing flange and the coupling in accordance with the configuration in the case of the plug-in coupling 131, in which case the media are guided in the laser hand piece to outlet openings associated with the treatment tool.

For the purpose of sealing the media when they pass through the cylindrical coupling gap, annular grooves 165 can be arranged on both sides of the annular grooves 154a, 154b or the radial channel sections 157a, 157b in the coupling bushing 137 or in the coupling peg 132, into which sealing rings, preferably O-rings 166, are inserted.

An articulated link-arm 108 described thus far, on account of its self-weight, is affected by a torque which is directed downwards and against which the operator has to act during the treatment when holding the laser treatment instrument 122 manually. In order to ease this, a compensating arrangement 171 is associated with the articulated link-arm 108, which arrangement at least in part compensates the self-weight of said arm in its starting position when it is deposited on the supporting portion 112 or in a central position of its range of movement, that is, counteracts the self-weight so that the articulated link-arm 108 is relieved of weight at least in part.

The articulated link-arm 108 is preferably arranged so that its rearmost arm link 108a or its leg 172 which points away radially relative to the axis of rotation 109a in its starting position extends obliquely towards the front (FIG. 7) or obliquely towards the rear (FIGS. 11 and 12) and thereby preferably extends downwards. The compensating arrangement 171 is formed and arranged so that it generates a torque at the rearmost arm link 108a counteracting the self-weight.

Figure 9:
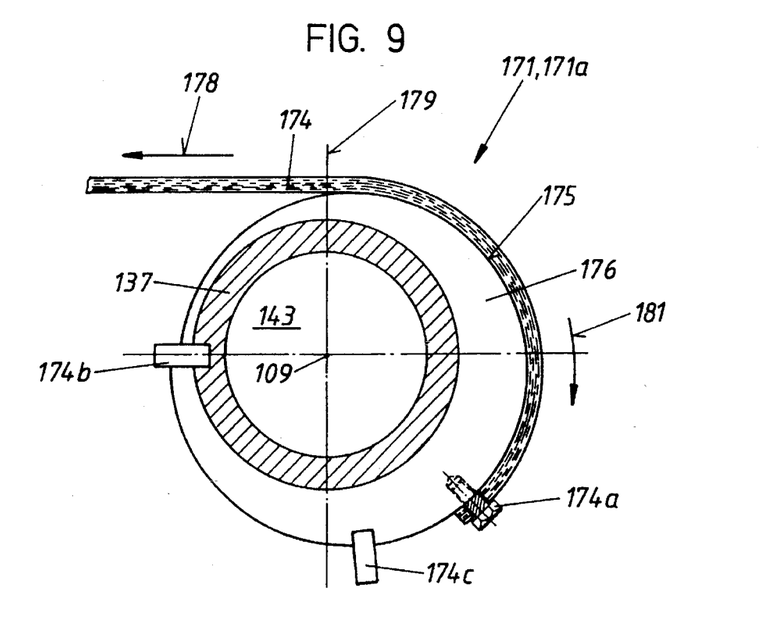
FIG. 9 shows a significant functional part of the compensating device in vertical section in IX—IX FIG. 3.
Figure 10:
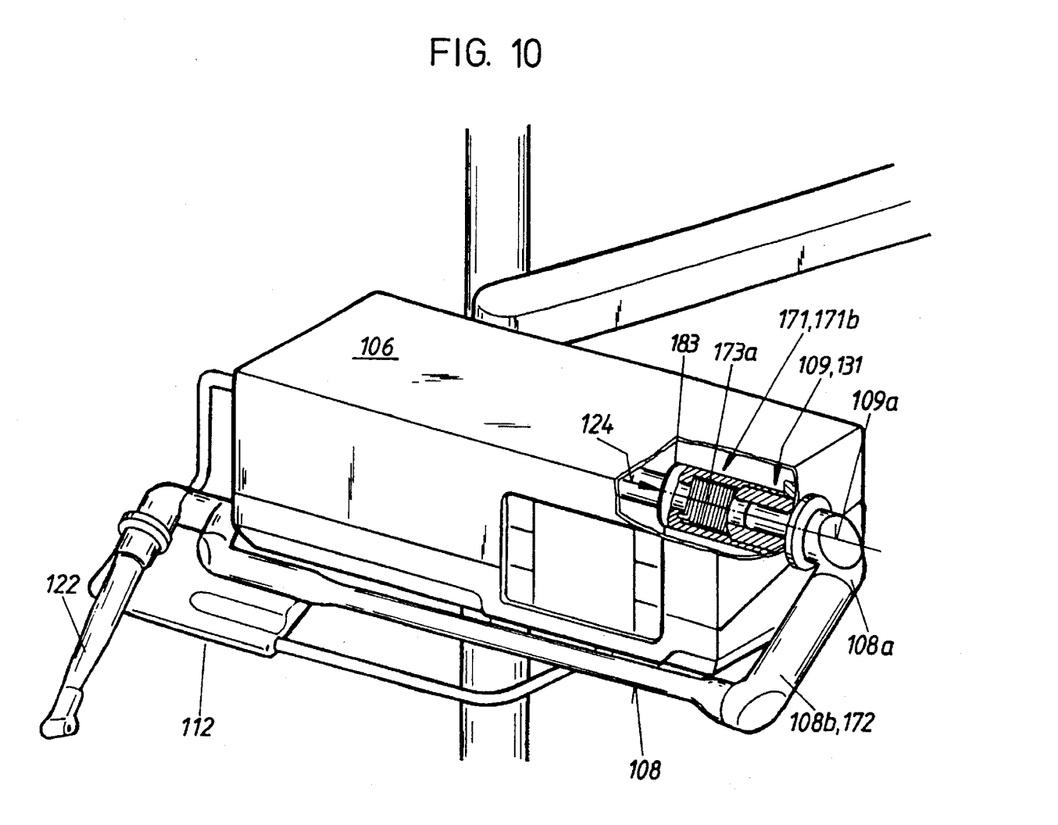
FIG. 10 shows a view corresponding to FIG. 7 with a modified weight-compensating device.

According to FIGS. 7, 9 and 10, a compensating arrangement 171a, 171b is provided which generates the compensating force, which is striven for, by means of a spring. The spring acts on the rearmost arm link 108a at a radial distance from the axis of rotation 109a, preferably at the coupling bushing 137. According to FIG. 7, a tension spring 173 is provided, which spring is supported on the housing 121 and acts directly or by means of a tension cable 174 on the coupling bushing 137. In order to ensure thereby a certain range of angle of rotation for the rearmost arm link 108a, the tension cable 174 is wound up over this certain range of angle of rotation on the periphery of the coupling bushing 137, preferably on the peripheral surface 175 of a flange 176, which in the case of the present configuration constitutes the rotary bearing portion. The tension cable 174 is secured at its tensioning end, for example by means of a screw 174a, at the coupling axis. The maximum movement of rotation produced by the compensating spring 173 can be limited by means of a stop or pin 174b which is secured to the coupling bushing 137 and which cooperates with a stop 174c which is secure with respect to the housing.

In order to be able to utilize the existing space better, in the case of the configuration according to FIG. 7 the tension spring 173 is arranged in the horizontal longitudinal direction of the housing 121, extending in an elongated manner parallel to the front side, therein preferably in the latter's rear region, in which case the tension cable 174 is deflected about a deflection roller 177 which is rotatably mounted on the housing 121.

Provided between the coupling bushing 137 and the plug-in peg 132 there is a rotary carrier connection 170 by means of which the compensating moment generated by the spring 173 can be transferred to the articulated link-arm 108. According to FIG. 8, the rotary carrier connection 170 is formed by means of several rotary carrier pins 170a which are arranged on a coaxial partial circle and which are set in rotary carrier holes 170b and thus likewise constitute a plug-in coupling which is automatically closed and opened when plugging in and unplugging the plug-in bolt 132. The rotary carrier pins 170a are preferably firmly inserted in axis-parallel holes of the flange 135 and they project therefrom towards the rear so as to be parallel to the axis in order to be able to be set into the pertinent rotary carrier holes 170b in the coupling bushing 137. One rotary carrier pin 170a suffices for a rotary carrier connection 170. Preferably several, for example four or six, rotary carrier pins 170a and pertinent rotary carrier holes 170b are arranged at the same angular intervals from each other. As a result, several coupling positions are created which are arranged so as to be staggered relative to each other in the peripheral direction. As a result, an adjusting arrangement for the magnitude of the spring force or of the compensating moment is created, because the rearmost arm link 108a can be coupled to the coupling bushing 137 in different positions of rotation and the pretension of the compensating spring and/or the initial position of rotation of the rearmost arm link 108a can thus be varied and selectively adjusted.

Figure 4:
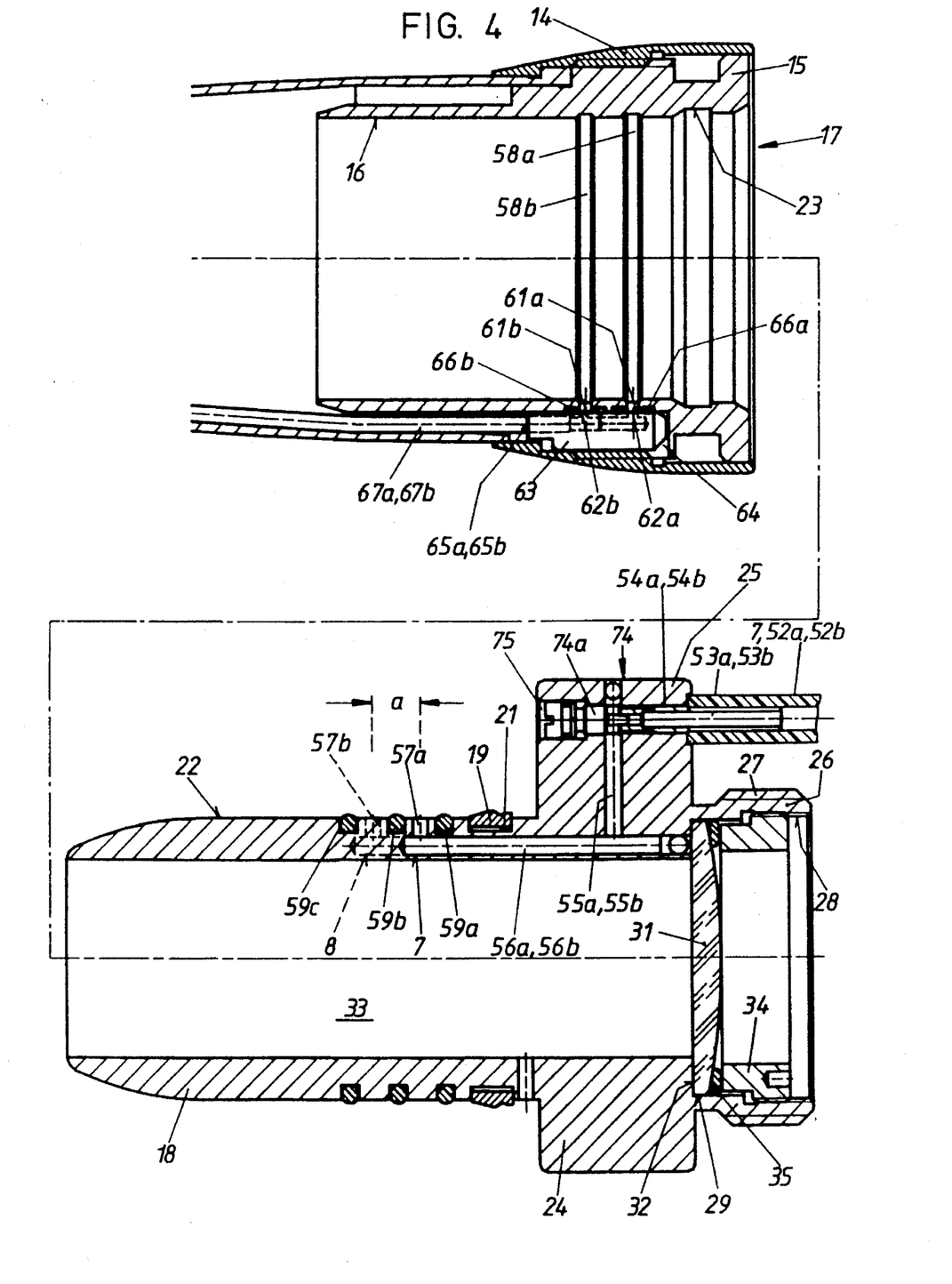
FIG. 4 shows an enlarged representation of the detail characterised in FIG. 1 by X in the uncoupled position.

It is advantageous to vary the compensating force illustrated with the arrow 178 as a function of the rotation of the rearmost arm link 108a so that it increases with increasing angular distance of the leg 172 from the vertical central plane 179. As a result variations in the self-weight torque 181 can be taken into consideration, which variations are effective on account of different inclined positions of the leg 172 and different effective distances 182 of a centre of gravity of the articulated link-arm 108 at least of the rearmost arm link 108a. This can be achieved in that the peripheral surface 175 has an eccentric or curve-shaped course which corresponds to the self-weight torques 181 effective in each case in different inclined positions of the leg 172 and different handling positions of the other arm links (FIG. 4).

As the operator holds the laser treatment instrument 122 in the hand and therefore carries a portion of the self-weight thereof, it is only necessary to counteract the remaining torque of the articulated link-arm 108 resulting from the remaining partial weight.

In the case of the configuration according to FIG. 10, the compensating spring is a torsion spring, in particular a spiral or helical spring 173a which is arranged coaxially relative to the axis of rotation 109a and is connected at its end facing the coupling bushing, in a manner secure with respect to rotation, with the coupling bushing 137 and at its end remote from the coupling bushing, in a manner secure with respect to rotation, with a supporting portion 183 which is fixed with respect to the housing. Axis-parallel angular ends of the helical spring can be used for this, which ends are set into axis-parallel holes of the coupling bushing 137 and of the supporting portion 183. The free inner cross section of the helical spring 173a has such large dimensions that the free passage of the laser beam 124 is not hindered. In the case of the configurations according to FIGS. 7 and 10, the compensating arrangement 171 is thus integrated into the control unit 106 or the housing 121 thereof respectively.

The compensating force of the compensating arrangement 171 can also be generated by a compensating weight. Such a configuration is provided according to FIGS. 11 and 12, in which the compensating arrangement 171 is arranged outside the control unit 106. In this case, a compensating weight 184 is provided, arranged in a releasable or non-releasable manner on the rear arm link 108a or preferably 108b. The effective distance 185 of the compensating weight 184 is selectively adjustable. A supporting rod 186 can be used for this, which in particular is radial and on which the compensating weight 184 is plugged with a hole and can be fixed, for example, by means of a clamping screw 187.

Figure 12:
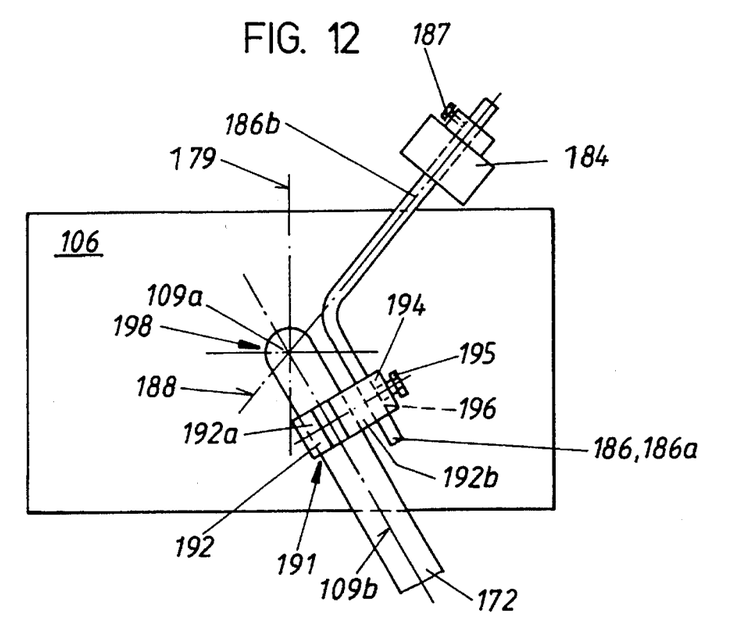
FIG. 12 shows significant individual parts of the weight-compensating device according to FIG. 11 in an enlarged representation.

FIG. 12 shows a holder 191 for the compensating weight 184 which, on the one hand, renders possible adjustability of the compensating weight 184 and, on the other hand, renders possible releasable securement on the leg 172. This holder 191 consists of a securing clip 192, the clip halves 192a, 192b of which can be firmly clamped by means of securing screws set in holes through them in a position in which they embrace the leg 172. A securing clip has a vertical hole 194, preferably in the form of a bore into which a supporting rod 186 which is bent off at an obtuse angle can be plugged with its vertical rod section 186a and can be firmly clamped in its vertical position, at which it is selectively plugged in, by means of a clamping screw 195, which can be screwed from the outside into a threaded bore hole 196 running into the hole 194. The supporting rod section 186b which in the installed position extends obliquely upwards is used to hold the compensating weight 184. In the case of this configuration, the compensating weight 184 can be adjusted by its adjustment on the supporting rod 186a, by an adjustment of the securing clip 192 along the leg 172 and by rotation of the supporting rod 186 in the hole 194.

In the case of this configuration, the compensating weight 184 is arranged in such a way that when swinging the arm link 108c, located in a substantially horizontal position of use, in and out, it is rotated as well, because the arm link 108b is likewise rotated as well about its longitudinal axis 109b. In the position in which the arm link 108c is swung out horizontally, the compensating weight is located in its rear position in which it exerts a large compensating torque and counteracts the increased torque of the articulated link-arm 108. When the arm link 108c is swung in towards the control unit 106, the compensating weight 184 is swung to the side, in which case its effective distance 185 is reduced. As a result, the effectiveness of the compensating weight 184 is automatically adapted as a function of the position of the arm link 108c and the torque of the articulated link-arm 108 which varies on the basis of this adjustment. In the position of the arm link 108c in which it is deposited on the supporting portion 112, the torque of the articulated link-arm 108 is small and the torque of the compensating weight 184 is also small, because it is swung to the side and towards the axis of rotation 109a. The arrangement, furthermore, is such that in the position of use of the articulated link-arm 108 or in the central position of the pertinent range of adjustment of the articulated link-arm 108, the longitudinal central axis 188 of the supporting rod 186 intersects the centre of gravity S of the articulated link-arm 108. The compensating weight 184 is located, relative to the vertical central plane 179, on the side towards which the leg 172 extends obliquely. If the latter extends obliquely downwards and preferably towards the rear, the supporting rod 186 extends obliquely upwards towards the rear.

Figure 11:
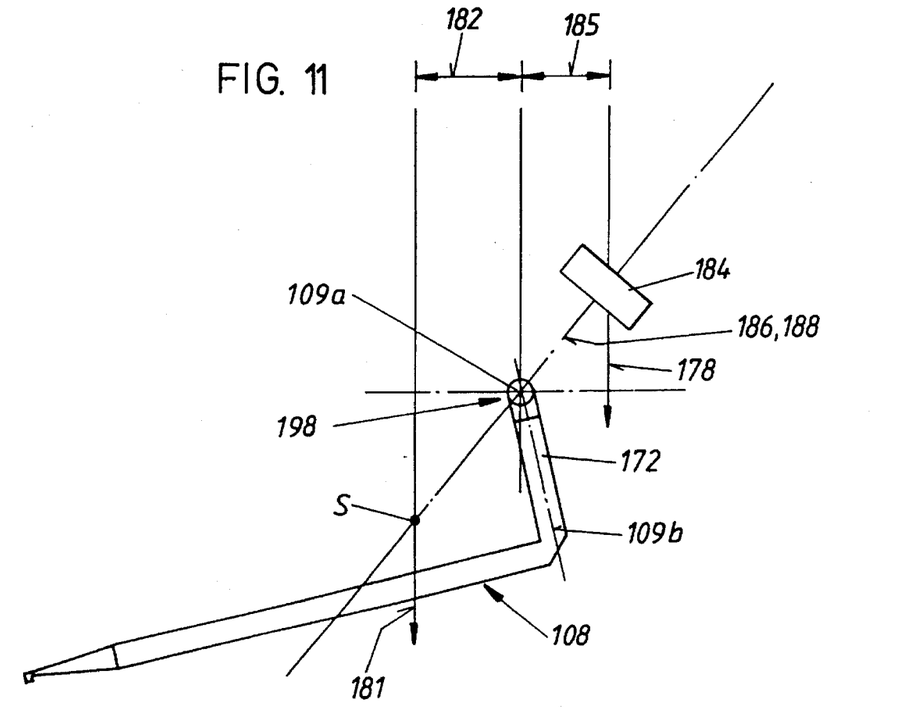
FIG. 11 shows the laser treatment unit with a further modified weight-compensating device in side view.

In the case of the exemplary embodiment according to FIGS. 11 and 12, a carrier arrangement 170 between the coupling bushing 137 and the plug-in or coupling peg 132 can be omitted and the coupling bushing 137 can be secured rigidly. On the other hand, it is advantageous to form the rearmost arm link 108a with two link portions which lie coaxially one after the other and which are rotatable about the axis of rotation 109a relative to each other. As a result, the coupling peg 132 is exempt from rotational movements when the articulated link-arm 108 is swung about the axis 109a (protection against wear). Such an articulation 198 can be integrated into the releasable connection between the coupling peg 132 and the arm link 108a carrying it.

The supporting portion 112 is preferably formed with a horizontal deposit surface 112a on which the free end region of the articulated link-arm 108 can be positioned in such a way that the treatment instrument 122 can also lie on the deposit surface 102a and thus can rest in a horizontal arrangement. The supporting portion 112 is therefore preferably formed in a plate-shaped manner. It is advantageous, furthermore, to associate with the supporting portion 112 a switch which ensures that only when the articulated link-arm 108 is lifted off from the supporting portion 112 is the unit ready to emit the laser beam 124 to the treatment instrument 122. Such a microswitch can be a pressure switch or a movement switch. The supporting portion 112 is preferably mounted such that it can move, or be swung, slightly vertically so that a movement switch can determine an automatic, for example, resilient upward movement of the supporting portion 112 when the articulated link-arm 108 is removed.

Figure 13:
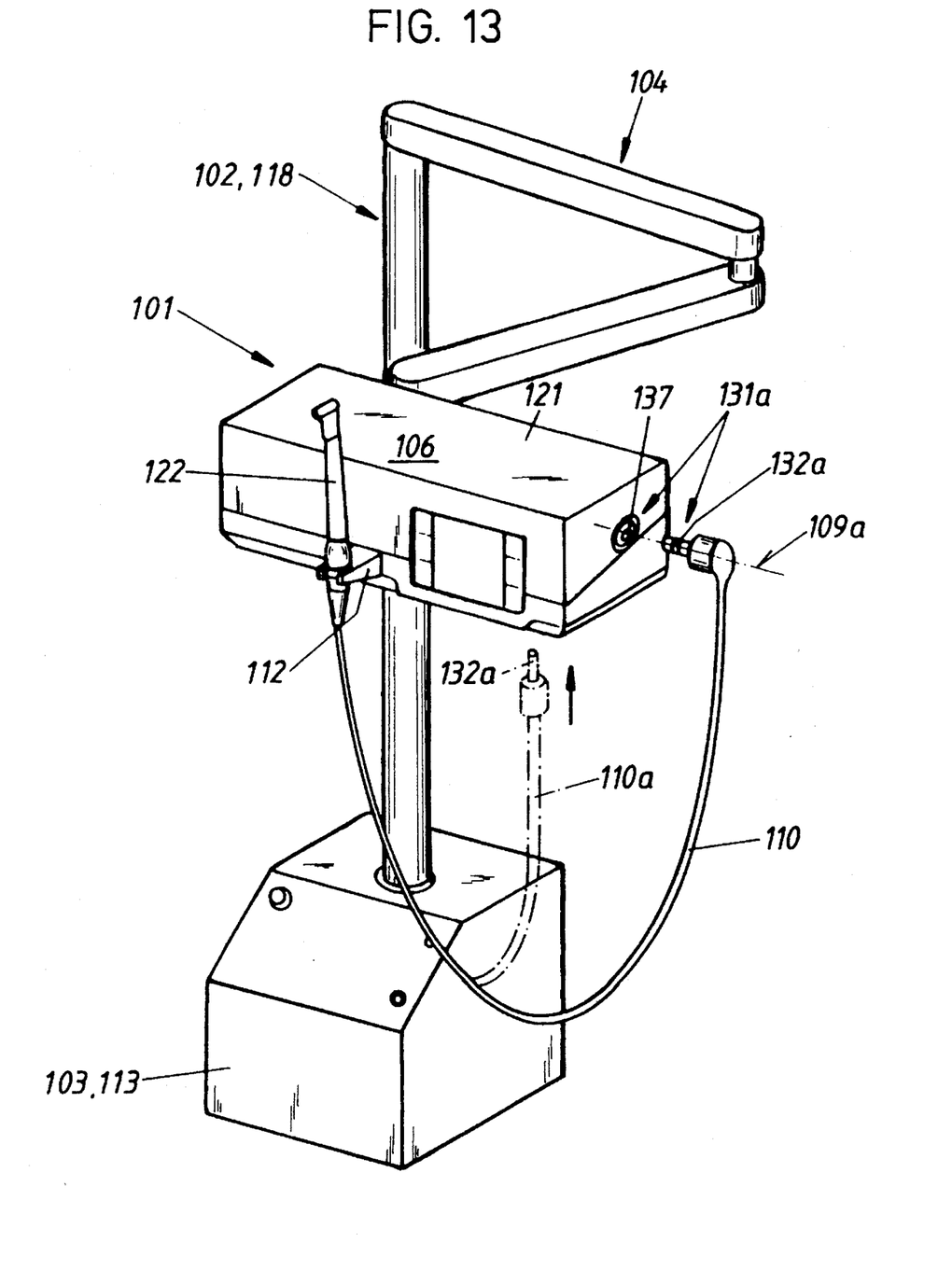
FIG. 13 shows a modified configuration of a dental laser treatment unit according to the invention in a perspective front view.

Within the scope of the invention it is possible to provide a different feed or supply device for media instead of an articulated link-arm 108. This can be a flexible light conductor cable 110. Such a light conductor cable is associated with the laser treatment unit 101 in FIG. 13, in which case it has at both ends a coupling element, with which it can be plugged with ease of operation and rapidly, on the one hand, onto the control unit 106 and, on the other hand, onto the laser treatment instrument 122. These two end coupling elements are preferably formed so as to be identical to each other so that each end of the flexible light conductor cable can be plugged both onto the control unit 106 and onto the laser treatment instrument 122. The plug-in/rotary couplings present can correspond to the configurations described above. A compensating arrangement is not present. The further media lines present can then extend within the light conductor cable 110 or on the outer periphery thereof. In the case of a lateral arrangement of the plug-in/rotary coupling 131a on the side of the unit according to FIG. 13, the light conductor cable 110 can continue axially onto the coupling peg 132a or it can be bent off by means of an angular section, as represented in FIG. 13.

A lateral arrangement of the plug-in/rotary coupling 131a on the side of the unit has the advantage—as already in the case of the previously described exemplary configurations—that when the light conductor cable 110 moves, as is necessary during treatment, the cable-side coupling peg 132a can rotate about its longitudinal axis 109a and thus be stressed less in respect of bending. It is, however, also possible within the scope of the invention to arrange the plug-in/rotary coupling on the underside of the control unit 6, preferably in the lateral and/or front end region of the existing housing. In the case of such an arrangement, the light conductor cable 110a first extends downwards and then in a curved manner upwards, in which case an angular section is not required for the light conductor cable 110a. Such a configuration is represented only schematically in FIG. 13.

The previously described light conductor cables can be of various designs. There are light conductor cables which have a light conductor channel filled with a fluid. It can also be a light conductor cable with a light conductor channel, the inner lateral surface of which is mirror-coated. It is also possible to use a flexible glass fibre cable.

In the case of all the previously described supply devices, the end-side coupling elements are preferably identical at least at one end, preferably at both ends, so that an articulated link-arm and previously described flexible cables conducting laser light can be exchanged one for the other. A great degree of efficiency of laser light transmission is guaranteed with the articulated link-arm. In the case of a glass fibre cable, a cable which has a laser light-conducting fluid, or a cable mirror-coated on the inside, the degree of efficiency is certainly less, yet simple handling is possible.

Moreover, all the aforementioned supply devices have various other disadvantages. A laser light conducting fluid tends, for example, to be become cloudy after a certain time.

Therefore in the case of all the supply devices described above, after certain intervals of time it is necessary to reckon on maintenance work or an exchange. This is simplified and facilitated by the presence of previously described rapid-action couplings.

In particular, identical formation of the rapid-action couplings results in inexpensive production and, moreover, the expense for stock-keeping is reduced.

Figure 14:
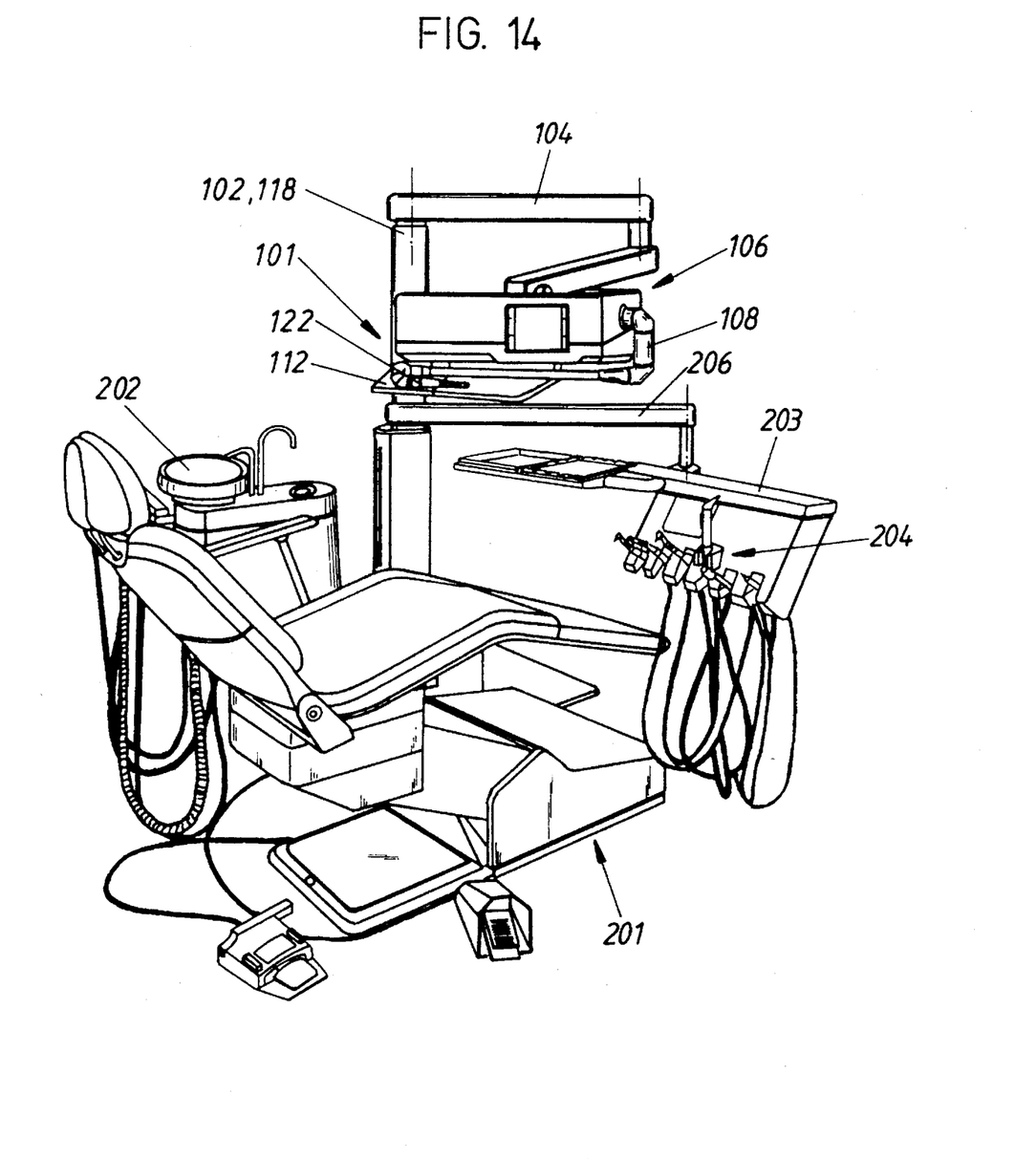
FIG. 14 shows a perspective representation of a dental treatment location with a treatment chair with which the laser treatment unit according to the invention is associated.

According to FIG. 14, the laser treatment unit 101 has associated therewith a dental treatment chair 201 with a standard rinsing basin arrangement 202 and a horizontally adjustable holder 203 for standard power-supplied treatment instruments 204. The holder 203, which is preferably provided with a deposit surface located thereon in a plate-shaped manner for non power-supplied treatment instruments, is mounted such that it can be swung preferably horizontally on a horizontal supporting arm 206 which is mounted likewise such that it can be swung horizontally below the supporting arm 104 for the control unit 106 on the supporting column 118. The supporting arm 106 is preferably mounted on the upper supporting column portion 118b and thus is likewise adjustable vertically.

What is claimed is:

1. A dental laser treatment unit comprising: a control unit; a supply device; a first releasable connection connecting the supply device with the control unit; a laser treatment instrument having a front end and an outlet at the front end for a laser beam; a second releasable connection connecting the laser treatment instrument with the supply device; at least first and second medium supply lines which issue from the control unit, extend through the first releasable connection, along the supply device, and through the second releasable connection to the laser treatment instrument, with the first medium line supplying a laser beam, and the second medium line supplying a fluid; wherein at least one of the first and second releasable connections comprises a cylindrical plug-in coupling, which engages and disengages elastically, having a cylindrical coupling peg and a cylindrical coupling bushing which receives the cylindrical coupling peg, with a cylindrical gap being defined between the cylindrical coupling peg and the cylindrical coupling bushing, and wherein the cylindrical coupling bushing is sealed by sealing means relative to the cylindrical coupling peg, with the first medium line for the laser beam extending coaxially through the at least one plug-in coupling, and the second medium line extending to an annular groove provided between the inner wall of the cylindrical coupling bushing and the outer wall of the cylindrical coupling peg, such that the cylindrical coupling peg can rotate by 360° and more relative to the cylindrical coupling bushing without interrupting the second medium line, and wherein the second medium line continues from said annular groove to the front end of the treatment instrument.

2. A dental laser treatment unit according to claim 1, wherein a said cylindrical coupling peg is provided at each end of the supply device and a said cylindrical coupling bushing is provided at the control unit and at the laser treatment instrument respectively.

3. A dental laser treatment unit according to claim 1, wherein each cylindrical plug-in coupling includes an engaging means which includes an elastic spring ring elastically seated in an annular groove recess arranged in the inner wall of the coupling bushing and the outer wall of the coupling peg, and in a coupled position the elastic spring ring engages an annular groove recess arranged adjacent to the elastic spring ring.

4. A dental laser treatment unit according to claim 1, wherein the first releasable connection includes a connection piece which is releasably connected with the supply device, and the connection piece has a connection element for the second medium line.

5. A dental laser treatment unit according to claim 4, wherein a third medium line is provided for an additional fluid, with one of the second and third medium lines supplying air and the other of the second and third medium lines supplying water.

6. A dental laser treatment unit according to claim 5, wherein the water medium line has an associated throttle valve arranged in the connection piece.

7. A dental laser treatment unit according to claim 6, wherein the throttle valve is arranged in a channel which is cut into the water medium line and includes a throttle valve member provided with a screw thread and an adjustment screw which is accessible for adjustment of the throttle valve.

8. A dental laser treatment unit according to claim 6, wherein a lens for the laser beam is arranged in the connection piece which is connected by a screw connection with the supply device, and the supply device includes at least one articulated link arm, and the lens is inserted into and fixed in a recess from a side which is remote from the cylindrical coupling peg.

9. A dental laser treatment unit according to claim 1, wherein the first and second releasable connections are identical to each other.

10. A dental laser treatment unit according to claim 9, including at least first and second different supply devices, the first supply device being an articulated link-arm, and the second supply device being a flexible cable for conducting laser light.

11. A dental laser treatment unit according to claim 10, wherein the flexible cable includes a channel with a fluid for conducting laser light.

12. A dental laser treatment unit according to claim 10, wherein the flexible cable includes a channel for conducting laser light, the inner lateral surface of which is mirror-coated.

13. A dental laser treatment unit according to claim 10, wherein the flexible cable includes at least one fiber optical line.

14. A dental laser treatment unit according to claim 1, wherein the first releasable connection is arranged with a substantially horizontal plug-in or coupling axis, and is provided laterally on a side of the control unit.

15. A dental laser treatment unit according to claim 1, wherein the first releasable connection is arranged with a substantially vertical plug-in or coupling axis and is provided underneath the control unit.

16. A dental laser treatment unit according to claim 1, wherein each plug-in coupling includes O-ring sealing means, arranged between the inner wall of the coupling bushing and the outer wall of the coupling peg, for sealing one or more medium lines.

17. A dental laser treatment unit according to claim 1, wherein both of the first and second releasable connections comprise a said plug-in coupling.

18. A dental laser treatment unit according to claim 1, wherein said annular groove is provided in the inner wall of the cylindrical coupling bushing.

19. A dental laser treatment unit according to claim 1, wherein said annular groove is provided in the outer wall of the cylindrical coupling peg.

20. A dental laser treatment unit according to claim 1, wherein said first releasable connection between the supply device and the control unit comprises a said cylindrical plug-in coupling, such that the supply device can rotate by 360° relative to the control unit without interrupting the second medium line.

21. A dental laser treatment unit according to claim 1, wherein said second releasable connection between the laser treatment instrument and the supply device comprises a said cylindrical plug-in coupling, such that the laser treatment instrument can rotate by 360° relative to the supply device without interrupting the second medium line.

* * * * *